(12) United States Patent
Andersen et al.

(10) Patent No.: US 7,623,914 B1
(45) Date of Patent: Nov. 24, 2009

(54) RECONFIGURABLE DIGITAL NETWORK FOR PROCESSING DATA IN AN IMPLANTABLE MEDICAL DEVICE

(75) Inventors: Dean Andersen, San Jose, CA (US); Cem Shaquer, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 495 days.

(21) Appl. No.: 11/104,240

(22) Filed: Apr. 11, 2005

(51) Int. Cl.
*A61N 1/00* (2006.01)

(52) U.S. Cl. .......................................... 607/2

(58) Field of Classification Search ................ 607/2–9, 607/30–32; 600/515; 128/903
See application file for complete search history.

(56) References Cited

U.S. PATENT DOCUMENTS

| | | | | |
|---|---|---|---|---|
| 5,050,065 | A | 9/1991 | Dartois et al. | 364/200 |
| 5,464,435 | A | 11/1995 | Neumann | 607/9 |
| 6,023,641 | A | 2/2000 | Thompson | 607/9 |
| 6,148,233 | A * | 11/2000 | Owen et al. | 607/5 |
| 6,167,303 | A | 12/2000 | Thompson | 607/2 |
| 6,185,454 | B1 | 2/2001 | Thompson | 607/2 |
| 6,185,460 | B1 | 2/2001 | Thompson | 607/16 |
| 6,223,080 | B1 | 4/2001 | Thompson | 607/16 |
| 6,266,554 | B1 * | 7/2001 | Hsu et al. | 600/515 |
| 6,389,315 | B1 | 5/2002 | Schu et al. | 607/16 |
| 6,415,181 | B1 | 7/2002 | Schu et al. | 607/16 |

| | | | | |
|---|---|---|---|---|
| 2003/0163298 | A1 | 8/2003 | Odom et al. | 703/21 |

FOREIGN PATENT DOCUMENTS

EP 1 259 288 B1 8/2004

OTHER PUBLICATIONS

Tessier, R. and Burleson, W., *Reconfigurable Computing for Digital Signal Processing: A Survey*, J. of VLSI Signal Processing 28: 7-27 (2001).
Donohoe, G. W. and Yeh, P., *A Reconfigurable Data Path Processor for Space Age Applications*, Proc. NASA Earth Sciences Technology Conference, University of Maryland (Aug. 29, 2001).
Donohoe, G.W. and Yeh, P., *A Low Power Reconfigurable Processor*, Proc. IEEE Aerospace Conference, Big Sky, MT (Mar. 9-16, 2002).

* cited by examiner

*Primary Examiner*—George Manuel
(74) *Attorney, Agent, or Firm*—Theresa A. Takeuchi; Steven M. Mitchell

(57) ABSTRACT

An implantable medical device (IMD) is provided. The IMD comprises a sense circuit, a main processing unit coupled to the sense circuit, a memory unit coupled to the main processing unit, and a reconfigurable processor unit coupled to the memory unit and the main processing unit. The reconfigurable processor unit is adapted to receive data, perform a processing function on the data, and return processed data to the memory unit. The memory unit is adapted to store the processed data. The main processing unit is adapted to execute programmed instructions and selectively reconfigure the processing function of the reconfigurable processor unit in response to one of the programmed instructions. Such a configuration can be used to implement a method of efficiently processing data in an IMD.

18 Claims, 7 Drawing Sheets

RECONFIGURABLE DIGITAL NETWORK FOR PROCESSING DATA IN AN IMPLANTABLE MEDICAL DEVICE

BACKGROUND OF THE INVENTION

1. Field of the Invention

The present invention relates generally to implantable medical devices. More specifically, the present invention relates to a reconfigurable digital network for use in an implantable medical device.

2. Background Art

An active implantable medical device is an apparatus, driven by a power source, which is implanted in a patient to monitor, detect, and possibly affect biological signals in the patient. Active implantable medical devices include, but are not limited to, implantable cardiac devices, implantable pressure transducers, and implantable drug delivery devices. The term "implantable medical device" or simply "IMD" is used herein to refer to any active implantable medical device known in the art.

Current IMD hardware platforms, using general purpose processors, are limited in their capability of performing general signal processing algorithms. Such a limitation is due to the fact that the longevity requirement of an IMD requires tight constraints on the number of clocks cycles and processing operations an IMD processor can perform. In other words, attempting to run very specific signal processing algorithms, for example, algorithms that perform many numerical computations on data, on current IMD processors, is a very inefficient use of the IMD's power. General purpose processors, however, do have the advantage of being highly programmable and reconfigurable.

To perform specific signal processing algorithms, it is well known that hardware designed specifically for the algorithm is more power efficient. Dedicated algorithm hardware, however, is not as reconfigurable as general purpose hardware. As such, dedicated algorithm hardware is suitable for only its dedicated function, but cannot be reprogrammed to perform different algorithms. What is needed is an IMD having a hardware architecture which can perform specific signal processing operations in a power efficient manner, while maintaining the reconfigurability of general purpose IMD hardware.

SUMMARY OF THE INVENTION

An implantable medical device (IMD) is provided. The IMD comprises a sense circuit, a main processing unit coupled to the sense circuit, a memory unit coupled to the main processing unit, and a reconfigurable processor unit coupled to the main processing unit and the memory unit. The reconfigurable processor unit is generally adapted to receive data from the memory unit, the main processing unit or the sense circuit. The reconfigurable processor is further adapted to perform a processing function on the data and return processed data to the memory unit. In one embodiment, the reconfigurable processor of the IMD comprises a plurality of individual processing units, each adapted to perform an individual processing function, wherein the plurality of individual processing units are linked in a reconfigurable network of individual processing units. Each individual processing unit is itself reconfigurable, to thereby reprogram its individual processing function. The processing function is typically a digital signal processing (DSP) operation, for example, discrete-time integration and differentiation, signal averaging, spectral analysis, and digital filtering.

The main processing unit is generally adapted to execute programmed instructions and selectively reconfigure the processing function of the reconfigurable processor unit in response to one of the programmed instructions. In one embodiment, the IMD may include a therapy circuit, coupled to the main processing unit, which is adapted to deliver an electro-therapy to the patient. In such an embodiment, the main processing unit receives processed data from the reconfigurable processor unit and selects an electro-therapy for delivery to the patient through the therapy circuit.

The IMD presented herein can be used in a method to efficiently process data. For instance, such a method includes the steps of directing data from the memory unit to the reconfigurable processor unit, via operation of the main processing unit. The reconfigurable processor then executes a DSP operation, while the main processing unit is switched to a low-power mode. After the reconfigurable processor performs the DSP operation, the data can be redirected to the main processing unit, or the memory unit. If necessary, the main processing unit can reconfigure the reconfigurable processor to perform a different DSP operation on the same or different data stream.

BRIEF DESCRIPTION OF THE FIGURES

The accompanying drawings, which are incorporated herein, form part of the specification and illustrate an IMD and method for efficiently processing data. Together with the description, the drawings further serve to explain the principles of and to enable a person skilled in the relevant art(s) to make and use the IMD presented herein. In the drawings, like reference numbers indicate identical or functionally similar elements.

DETAILED DESCRIPTION OF THE INVENTION

The following detailed description of the accompanying drawings illustrates example embodiments of an implantable medical device (IMD) for efficient data processing. Other embodiments are possible, and modifications may be made to the embodiments within the spirit and scope of the IMD presented herein. Therefore, the following detailed description is not meant to limit the IMD. Rather, the scope of the IMD is defined by the appended claims.

It would be apparent to one of skill in the art that the IMD, as described below, may be implemented in many different embodiments of hardware, software, firmware, and/or the entities illustrated in the figures. Any actual software and/or hardware described herein is not limiting of the IMD presented herein. Thus, the operation and behavior of the IMD will be described with the understanding that modifications and variations of the embodiments are possible, given the level of detail presented herein.

The IMD presented herein is particularly useful in the environment of an implantable cardioverter defibrillator (ICD). An ICD is a medical device that is implanted in a patient to monitor the electrical activity of a heart and to deliver appropriate electrical therapy; for example, pacing pulses, cardioverting pulses, or defibrillating (or shock) pulses, as required. The term "implantable cardioverter defibrillator" or simply "ICD" is used herein to refer to any implantable cardiac device known in the art. Hereinafter, the IMD apparatus presented shall be described in the environment of an ICD. It should be noted that the IMD defined by the appended claims is not limited to use solely in an ICD, but is described in an the environment of an ICD for simplicity.

Figure 1:
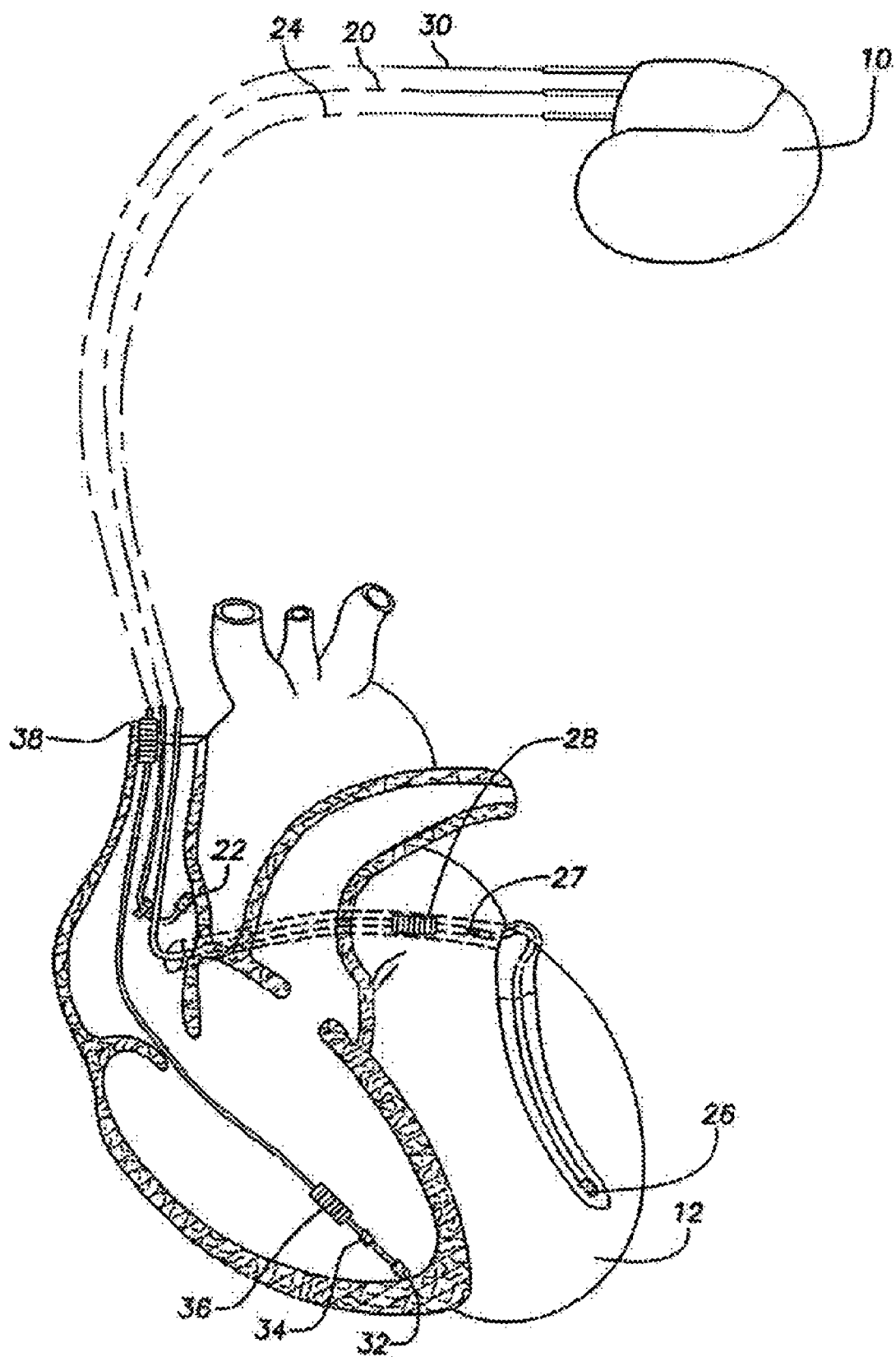
FIG. 1 is a simplified diagram illustrating an exemplary IMD in electrical communication with a patient's heart.

FIG. 1 illustrates an exemplary ICD 10 in electrical communication with a patient's heart 12 by way of three leads 20, 24 and 30, suitable for delivering multi-chamber stimulation and pacing therapy. To sense atrial cardiac signals, and to provide right atrial chamber stimulation therapy, ICD 10 is coupled to implantable right atrial lead 20, having at least an atrial tip electrode 22, which typically is implanted in the patient's right atrial appendage.

To sense left atrial and ventricular cardiac signals, and to provide left-chamber pacing therapy, ICD 10 is coupled to "coronary sinus" lead 24. Lead 24 is designed for placement in the "coronary sinus region," via the coronary sinus, for positioning of a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein, or any other cardiac vein accessible by the coronary sinus. Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shock therapy using at least a left atrial coil electrode 28.

ICD 10 is also shown in electrical communication with the patient's heart 12 by way of an implantable right ventricular (RV) lead 30 having, in this embodiment, a RV tip electrode 32, a RV ring electrode 34, a RV coil electrode 36, and a superior vena cava (SVC) coil electrode 38. Typically, RV lead 30 is transvenously inserted into heart 12 so as to place the RV tip electrode 32 in the right ventricular apex so that RV coil electrode 36 will be positioned in the right ventricle and SVC coil electrode 38 will be positioned in the superior vena cava. Accordingly, RV lead 30 is capable of receiving cardiac signals and delivering stimulation in the form of pacing and shock therapy to the right ventricle. Other embodiments of ICD 10 may include a single electrode and lead or one or more alternative combinations of the above mentioned electrode and lead configurations.

Amongst other things, any one of, or any combination of, leads 20, 24, and 30, functions as a sense circuit to sense an electrogram (EGM) signal from the heart 12. The EGM signal is then processed within the ICD 10, as discussed below. The sense circuit, with respective electrodes, thereby serves as means for sensing one or more electrical signals from the patient's heart 12. Further, any one of, or any combination of the leads 20, 24, and 30, in part, function as a therapy circuit to deliver a selected electro-therapy to the heart 12. The therapy circuit, with respective electrodes, thereby serves as means for delivering an electro-therapy to the heart 12.

The selected electro-therapy can be, but is not limited to, anti-tachycardia pacing (ATP) therapy, or shock therapy. If ATP therapy is selected, a pre-programmed series of burst pulses is sent to the heart through any one of, or any combination of, leads 20, 24, and 30. There are several different ATP modalities which have been suggested for termination of tachycardia. Some examples of patent documents which discuss ATP therapies are U.S. Pat. No. 6,731,982, U.S. Pat. No. 4,408,606, U.S. Pat. No. 4,398,536, U.S. Pat. No. 4,488,553, U.S. Pat. No. 4,488,554, U.S. Pat. No. 4,390,021, U.S. Pat. No. 4,181,133 and U.S. Pat. No. 4,280,502, the disclosures of which are hereby incorporated in their entireties by reference.

Figure 2:
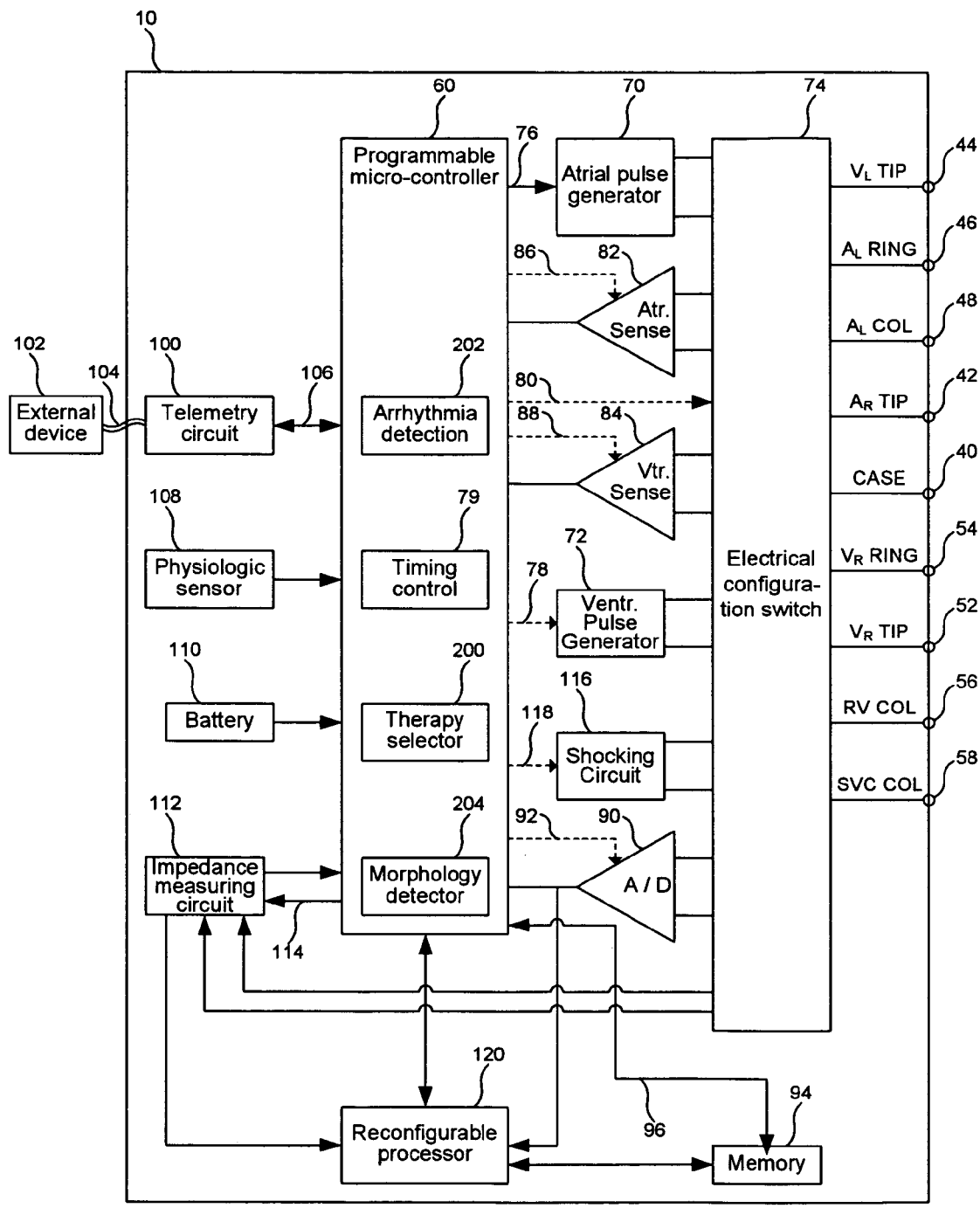
FIG. 2 is a functional block diagram of an exemplary IMD that can provide, amongst other things, cardioversion, defibrillation, and pacing stimulation in three chambers of a heart.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes 28, 36, and 38, for shocking purposes. Housing 40 further includes a connector (not shown) having a plurality of terminals 42, 44, 46, 48, 52, 54, 56, and 58. These terminals are shown schematically and, for convenience, the names of the electrodes to which they are connected are shown next to the terminals. For example, to achieve right atrial sensing and pacing, the connector includes a right atrial tip terminal ($A_R$ TIP) 42 adapted for connection to atrial tip electrode 22.

To achieve left chamber sensing, pacing, and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to left ventricular tip electrode 26, left atrial ring electrode 27, and left atrial coil electrode 28, respectively.

To support right chamber sensing, pacing, and shocking, the connector also includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a main processing unit, referred to as programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Known microcontrollers include the ability to process or monitor input data, such as biological signals, as controlled by a program code stored in a designated block of memory. In ICD 10, however, a reconfigurable processor 120, as described below, is used to process such data. Instead, microcontroller 60 serves as a general processing means for executing general operational functions within ICD 10. The details of the design of microcontroller 60 are not critical to the present invention. Rather, any suitable microcontroller 60 can be used to carry out the functions described herein.

Representative types of control circuitry that may be used with the invention include the microprocessor-based control system of U.S. Pat. No. 4,940,052 (Mann et al.) and the state-machines of U.S. Pat. Nos. 4,712,555 (Sholder) and 4,944,298 (Sholder). For a more detailed description of the various timing intervals used within ICDs, and their interrelationship, see U.S. Pat. No. 4,788,980 (Mann et al.). The '052, '555, '298 and '980 patents are incorporated herein by reference in their entireties.

Microcontroller 60 includes a timing control circuitry 79, which is used to control pacing parameters (e.g., the timing of stimulation pulses, the burst pacing parameters, etc.) as well as to keep track of the timing of refractory periods, post ventricular atrial refractory period intervals, noise detection windows, evoked response windows, alert intervals, marker channel timing, etc., which are well known in the art. Examples of pacing parameters include, but are not limited to, atrio-ventricular delay, interventricular delay, atrial interconduction delay, ventricular interconduction delay, and pacing rate.

Microcontroller 60 also includes a therapy selector unit 200, which serves as means for selecting an appropriate electro-therapy for delivery to the heart. The appropriate therapy can be selected from a plurality of therapies. For example, ATP therapy can be used. Alternative therapies include shock therapy, or any other electro-therapies known in the art.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses.

Switch block 74 includes a plurality of switches for connecting the desired electrodes to the appropriate I/O circuits, thereby providing complete electrode programmability. Accordingly, switch block 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch block 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch block 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60, which in turn is able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 84.

For arrhythmia detection, ICD 10 utilizes the atrial and ventricular sensing circuits 82 and 84 to retrieve EGM signals from the heart. The EGM signals are then analyzed in the arrhythmia detection unit 202 of the microcontroller 60. If an arrhythmia is detected, typically based on heart rate, the arrhythmia can then be classified by morphology detector unit 204. If additional data processing is needed, the data can be transferred to reconfigurable processor 120, wherein a specific DSP operation is executed in a power-efficient manner. For example, reconfigurable processor 120 can be used to perform DSP operations such as discrete-time integration and differentiation, signal averaging, spectral analysis, and digital filtering.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing in microcontroller 60, reconfigurable processor 120, and/or telemetric transmission to an external device 102. Data acquisition system 90 is coupled to right atrial lead 20, coronary sinus lead 24, and right ventricular lead 30, through switch 74, to sample cardiac signals across any pair of desired electrodes.

Advantageously, data acquisition system 90 can be coupled to microcontroller 60, reconfigurable processor 120, or other detection units, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90, via a control signal 92, to sample the cardiac signal that falls in the capture detection window and, based on the amplitude, determine if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which patents are hereby incorporated in their entireties herein by reference. The type of capture detection system used is not critical to the present invention.

Microcontroller 60 is further coupled to a memory unit 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to heart 12 within each respective tier of therapy. The memory unit 94 thus serves as means for "learning" which therapies are most effective under certain conditions. As such, when a condition repeats itself, the memory can recognize the condition and adapt the selected therapy to match the previously used successful therapy.

Advantageously, the operating parameters of ICD 10 may be non-invasively programmed into memory unit 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104. Telemetry circuit 100 also serves as a means for receiving parameters from an outside programmer, to thereby program the reconfigurable processor 120, via operation of microcontroller 60.

For examples of external devices, such as external device 102, see U.S. Pat. No. 4,809,697 (Causey, III et al.); U.S. Pat. No. 4,944,299 (Silvian); and U.S. Pat. No. 6,275,734 (Mc-Clure et al.); all patents being hereby incorporated in their entireties herein by reference.

Memory unit 94 is also coupled to reconfigurable processor 120. As such, reconfigurable processor 120 is adapted to receive data from memory unit 94, perform a processing function on the data, and return processed data to memory unit 94. Such operations are generally programmed and supervised by operation of microcontroller 60. In other words, microcontroller 60 can reconfigure the internal parameters of reconfigurable processor 120, to thereby modify the processing function of reconfigurable processor 120. As such, the microcontroller 60 serves as general processing means for executing general operational functions, while the reconfigurable processor 120 serves as reconfigurable processing means for performing DSP operations. Such a configuration has the advantage of allowing reconfigurable processor 120 to process the data while microcontroller 60 is switched to a low-power mode, thus improving the efficiency of ICD 10.

ICD 10 further includes a physiologic sensor 108 that can be used to detect changes in cardiac performance or changes in the physiological condition of the heart. Accordingly, microcontroller 60 can respond by adjusting the various pacing parameters (such as amplitude, rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

ICD 10 may further include a magnet detection circuitry (not shown), coupled to microcontroller 60. The magnet detection circuitry detects when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 is shown as having an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement, detecting operable electrodes and automatically switching to an operable pair if dislodgement occurs, measuring respiration or minute ventilation, measuring thoracic impedance for determining shock thresholds, detecting when the device has been implanted, measuring stroke volume, and detecting the opening of heart valves. The impedance measuring circuit 112 is advantageously coupled to switch 74 so that any desired electrode may be used. Impedance measuring circuit 112 is also coupled to reconfigurable processor 120, wherein outputs from impedance measuring circuit 112 can be processed and stored in memory unit 94. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. Shocking circuit 116 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV coil electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognized), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Figure 3:
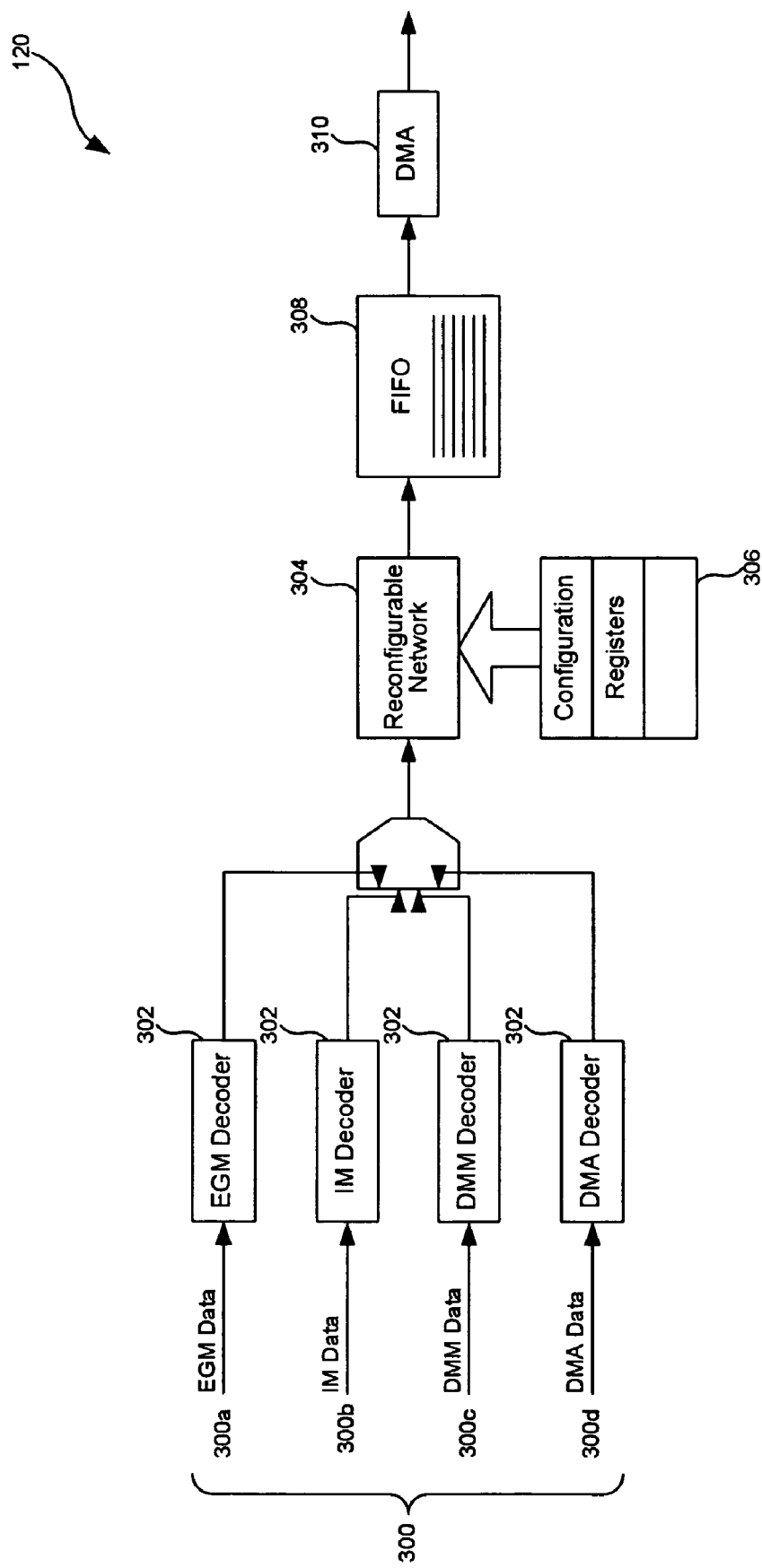
FIG. 3 is a block diagram of an exemplary reconfigurable processor unit.

FIG. 3 illustrates a block diagram of an exemplary reconfigurable processor 120. Input data 300, such as biological signals (EGM Data) 300*a*, impedance (IM) data 300*b*, digital multi-meter (DMM) data 300*c*, or digital memory access (DMA) data 300*d*, enters reconfigurable processor 120 through decoders 302. DMM data 300*c* includes status data of ICD 10, such as, for instance, battery voltage. The data types listed and shown in FIG. 3 are not intended to be limiting. For example, reconfigurable processor 120 is adapted to process additional data types, such as pressure data or activity data.

Decoders 302 select the desired data to be processed. The data is then processed in reconfigurable network 304, as further described below. Reconfigurable network 304 executes the desired processing function, which is set by configuration registers 306. Configuration registers 306, in turn, are programmed by microcontroller 60. As such, the combination of microcontroller 60 and configuration registers 306 serves as a reconfiguration means for programming internal parameters of the reconfigurable network 304. Once the data is processed, it is transferred to memory unit 94 through "first-in-first-out" (FIFO) 308 and direct memory access (DMA) 310 structures.

Figure 4:
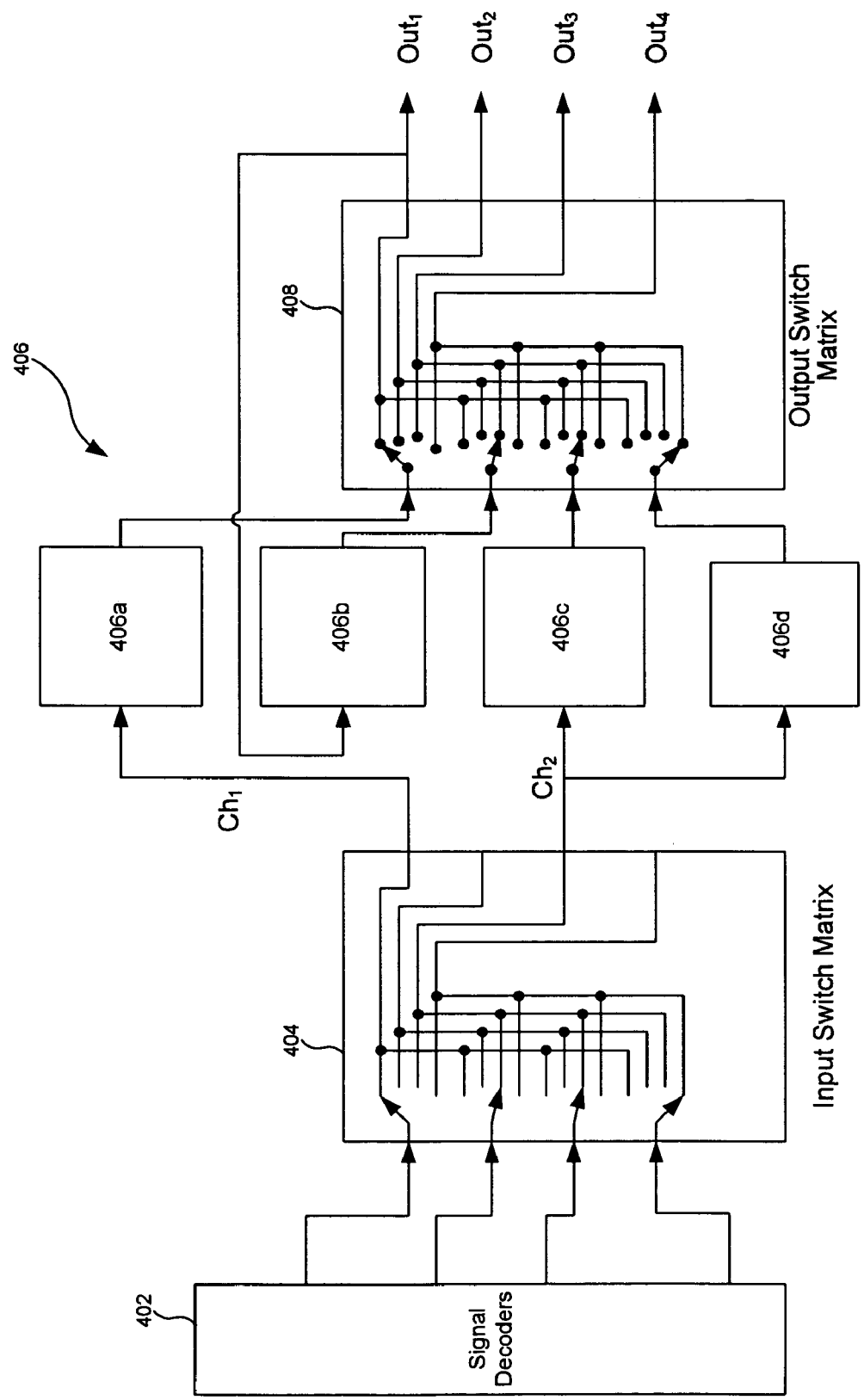
FIG. 4 is a diagram of an exemplary reconfigurable network.

FIG. 4 is a diagram of an exemplary reconfigurable network 304. Reconfigurable network 304 is comprised of signal decoders 402, an input switch matrix 404, a plurality of individual processing units 406, and an output switch matrix 408. In the embodiment shown in FIG. 4, four processing units 406 are implemented. Processing units 406a and 406b are connected in series using the signal from $Ch_1$ as an input. The output from processing unit 406a goes into the input of processing unit 406b. Processing units 406c and 406d receive inputs from $Ch_3$, but are assigned to separate outputs, $Out_3$ and $Out_4$ respectively. The assignments of input signals and output signals are all reconfigurable by inputs from microcontroller 60. Further, microcontroller 60 controls how the individual processing units are configured and connected to one another.

Figure 5:
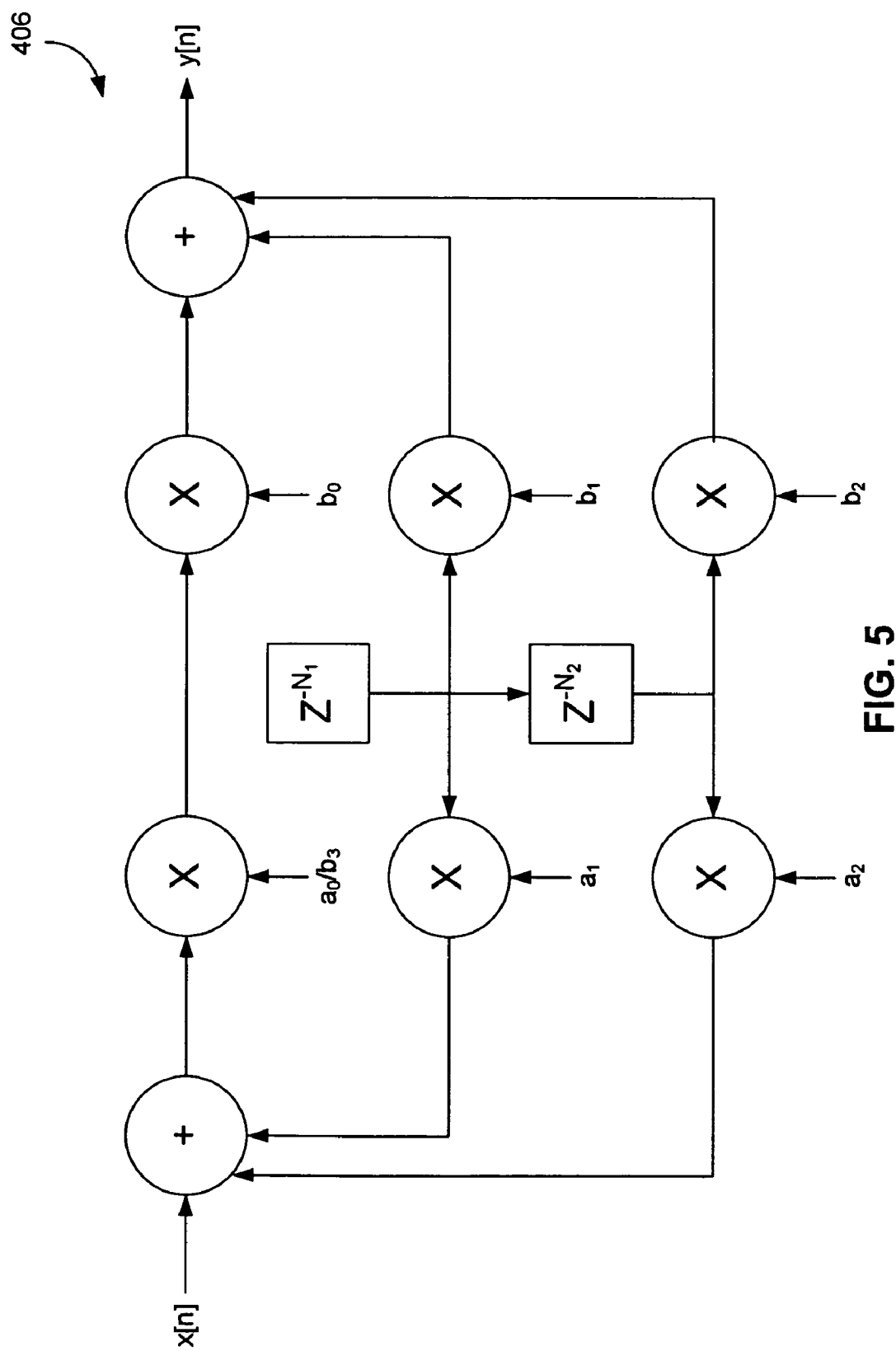
FIG. 5 is a simplified diagram of an exemplary individual processing unit.
Figure 6:
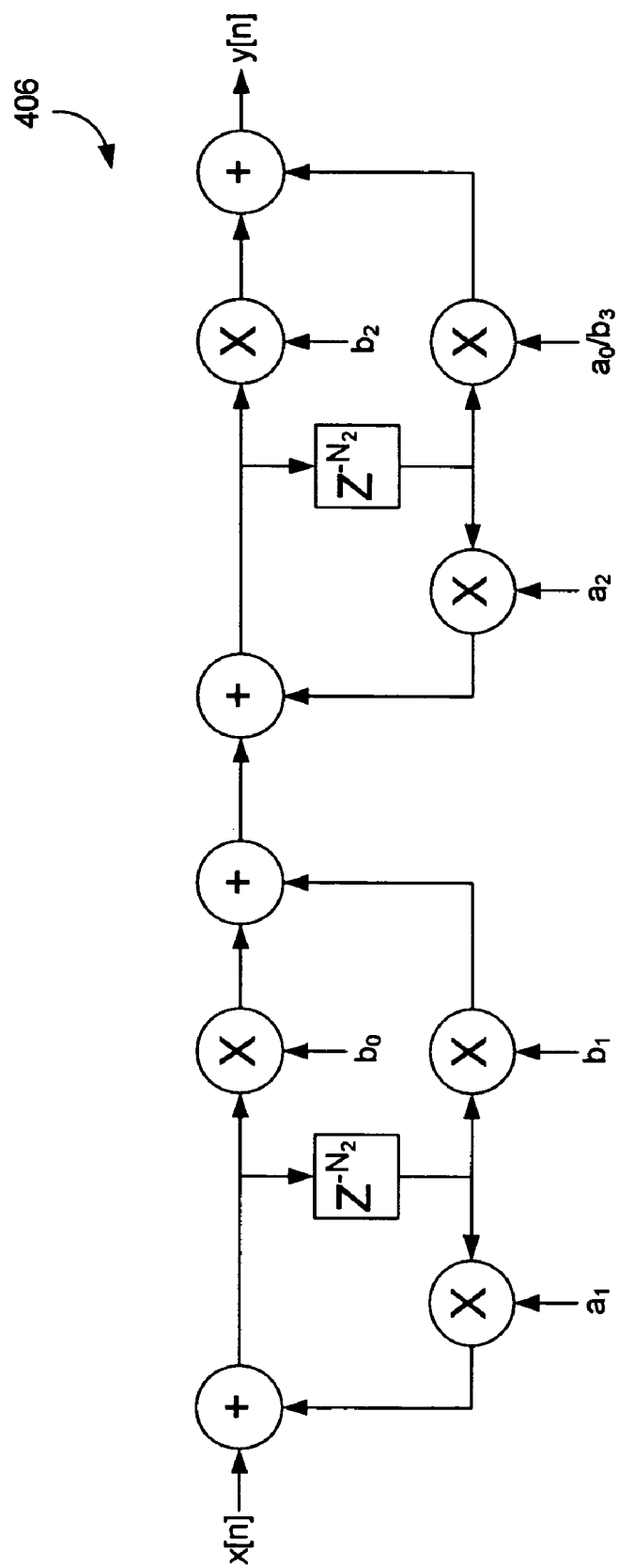
FIG. 6 is a simplified diagram of an alternative individual processing unit.

FIG. 5 is a simplified diagram of an exemplary individual processing unit 406. The structure shown in FIG. 5 is a parallel structure, realizing a direct-form second order digital filter. FIG. 6 is a simplified diagram of an alternative individual processing unit 406. The structure shown in FIG. 6 is a cascade implementation, realizing two direct-form first order filters. Processing units 406, of reconfigurable network 304, are thus based on direct-form filter structures, wherein the coefficients are programmable and reconfigurable, to thus enable the realization of a wide variety of digital filters. As will be evident to those skilled in the art, the network includes six multipliers and two delay elements. The coefficients ($a_x$ and $b_x$) and the delay values ($N_x$) can be adjusted to customize the desired DSP operation. As such, the digital input ($x[n]$) can be processed into a digital output ($y[n]$).

In this manner, DSP operations, which require slow clock speeds, can be performed in reconfigurable processor 120, instead of microcontroller 60. As such, the data is processed in a more efficient manner. Microcontroller 60, which typically runs at fast clock speeds, can thus be turned to a low-power mode while reconfigurable processor 120 executes the DSP operations. The term "slow clock speeds" means clock speeds that are generally less than 100 kHz, while the term "fast clock speeds" means clock speeds that are generally greater than 1 MHz. The "slow clock speed" is generally determined by the sample rate of the data being processed. A slow clock speed is usually much slower than the speed at which microcontroller 60 is operating.

Figure 7:
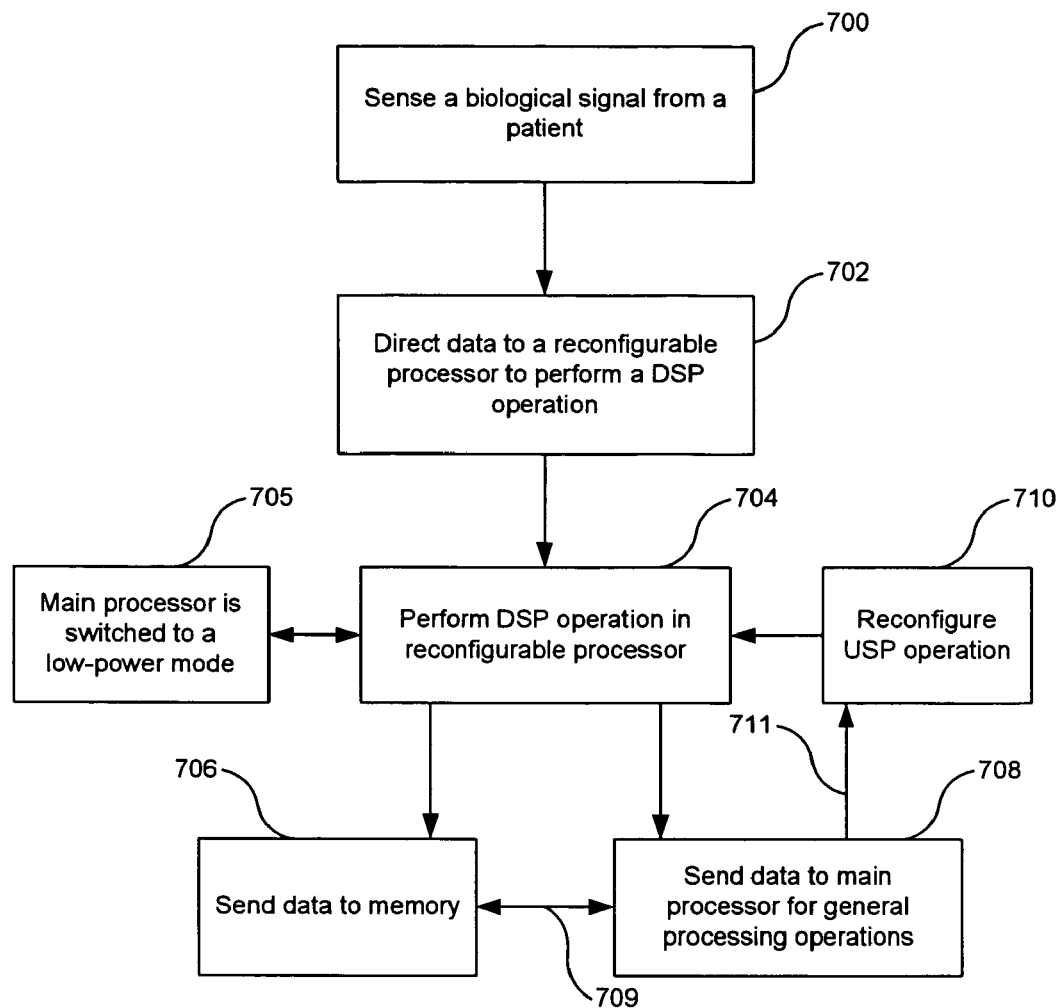
FIG. 7 is a flowchart depicting a method of efficiently processing biological data, using the IMD presented herein.

FIG. 7 is a flowchart depicting a method of efficiently processing data, using an IMD, such as the ICD 10 presented herein. In step 700, a biological signal is sensed from the patient using the sensing means described above. In the embodiment depicted in FIG. 7, the sensed biological signal is the data to be processed. In step 702, the data is directed to a reconfigurable processor, such as reconfigurable processor 120, to perform a DSP operation. Reconfigurable processor 120 can receive data from memory unit 94, the main processing unit, or directly from the sense circuit. The DSP operation is performed in step 704. While reconfigurable processor 120 performs the DSP operation, the main processor is switched at step 705 to a low-power mode to conserve energy. The reconfigurable processor can then send the data directly to the memory unit in step 706, or it can send the data to the main processor, such as microprocessor 60, for general processing operations in step 708. The data can also be transferred between the main processor and the memory through the data communication link 709. If necessary, the main processor can communicate with the reconfigurable processor in step 710, through link 711, to reconfigure the DSP operation performed by the reconfigurable processor.

CONCLUSION

Example embodiments of an IMD for efficient data processing have been described. As noted elsewhere, these example embodiments have been described for illustrative purposes only, and are not limiting. Other embodiments are possible and are covered by IMD described herein. Such embodiments will be apparent to persons skilled in the relevant art(s) based on the teachings contained herein.

What is claimed is:

1. An implantable medical device (IMD) comprising:
a sense circuit;
an implantable main processing unit coupled to the sense circuit and adapted to execute general operational functions within the IMD;
a memory unit coupled to the implantable main processing unit and adapted to store processed data; and
an implantable reconfigurable processor unit coupled to the implantable main processing unit and adapted to receive data, perform a processing function on the data, and return processed data to the memory unit, wherein the implantable main processing unit is adapted to selectively reconfigure the coefficient of the reconfigurable processor unit in response to a programmed instruction.

2. The IMD of claim 1 wherein the reconfigurable processor further comprises:
a plurality of processing units, each adapted to perform a processing function, wherein the plurality of processing units are linked in a reconfigurable network, and wherein each processing unit is itself reconfigurable, to thereby reprogram its processing function and wherein the implantable main processing unit is configured to control how individual processing units are configured and connected to one another.

3. The IMD of claim 2 wherein the plurality of processing units are linked in series, in parallel, or in a combination of series and parallel connections.

4. The IMD of claim 2 wherein the reconfigurable network further comprises an input switch matrix and an output switch matrix which link the plurality of processing units in the reconfigurable network, and wherein the implantable main processing unit is adapted to reconfigure the assignment of input signals and output signals of the reconfigurable network.

5. The IMD of claim 1 further comprising:
a therapy circuit coupled to the main processing unit and adapted to deliver an electro-therapy to a patient, wherein the main processing unit is adapted to receive processed data from the reconfigurable processor unit and select the electro-therapy for delivery to the patient based on the processed data.

6. The IMD of claim 1 wherein the main processing unit is adapted to run at a clock speed greater than a clock speed of the reconfigurable processor unit.

7. The IMD of claim 1 wherein the processing function is digital filtering.

8. The IMD of claim 1 wherein the processing function is spectral analysis.

9. The IMD of claim 1 wherein the processing function is a digital signal processing (DSP) operation comprising at least one of discrete-time integration and differentiation, signal averaging, spectral analysis, and digital filtering.

10. The IMD of claim 1 wherein the implantable main processing unit is further adapted to selectively reconfigure the delay values of the reconfigurable processor unit in response to a programmed instruction.

11. A method of processing data in an implantable medical device (IMD) comprising:
with an implantable main processing unit of the IMD selectively reconfiguring the coefficient and delay values of a reconfigurable processor unit of the IMD;
directing data to the reconfigurable processor unit, via operation of the implantable main processing unit, to perform a digital signal processing (DSP) operation;
switching the implantable main processing unit into a low-power mode; and
performing the DSP operation, via operation of the reconfigurable processor unit, while the implantable main processing unit is in the low-power mode.

12. The method of claim 11, further comprising:
running the reconfigurable processor unit at a slower clock speed than a clock speed of the main processing unit.

13. The method of claim 11, further comprising:
programming the reconfigurable processor unit, via operation of the main processing unit, to perform the DSP operation.

14. The method of claim 13, further comprising:
reconfiguring the reconfigurable processor unit, via operation of the main processing unit, to perform a different DSP operation.

15. The method of claim 11, further comprising:
programming the reconfigurable processor unit, via operation of the main processing unit, to perform the DSP operation, wherein the DSP operation comprises at least one of discrete-time integration and differentiation, signal averaging, spectral analysis, and digital filtering.

16. An implantable medical device (IMD) comprising:
sensing means for sensing data;
an implantable general processing means, coupled to the sensing means, for executing general operational functions within the IMD;
memory means, coupled to the general processing means, for storing the data;
an implantable reconfigurable processing means, reconfigurable by the general processing means and coupled to the general processing means, for performing a digital signal processing (DSP) operation on the data; and
reconfiguration means, coupled to the reconfigurable processing means, for programming coefficients of the reconfigurable processing means to thereby program the DSP operation.

17. The IMD of claim 16, further comprising:
telemetry means, coupled to the reconfiguration means, for receiving parameters from an outside programmer, to thereby program the reconfigurable processing means.

18. The IMD of claim 16, wherein the DSP operation comprises at least one of discrete-time integration and differentiation, signal averaging, spectral analysis, and digital filtering.

* * * * *

UNITED STATES PATENT AND TRADEMARK OFFICE
CERTIFICATE OF CORRECTION

PATENT NO. : 7,623,914 B1
APPLICATION NO. : 11/104240
DATED : November 24, 2009
INVENTOR(S) : Andersen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 809 days.

Signed and Sealed this

Twenty-sixth Day of October, 2010

David J. Kappos
*Director of the United States Patent and Trademark Office*